United States Patent [19]

Yamanaka

[11] Patent Number: 5,101,382
[45] Date of Patent: Mar. 31, 1992

[54] ACOUSTIC IMAGING METHOD AND APPARATUS FOR NONDESTRUCTIVE EVALUATION OF MATERIALS

[75] Inventor: Kazushi Yamanaka, Tsukuba, Japan

[73] Assignees: Agency of Industrial Science & Technology; Ministry of International Trade & Science, Tokyo, Japan

[21] Appl. No.: 603,553

[22] Filed: Oct. 26, 1990

[30] Foreign Application Priority Data

Nov. 2, 1989 [JP] Japan .................. 1-286076

[51] Int. Cl.$^5$ .................. G03B 42/06; G01N 29/00
[52] U.S. Cl. .................. 367/7; 73/644
[58] Field of Search .................. 367/7; 73/597–600, 73/620, 644, 629, 571

[56] References Cited

U.S. PATENT DOCUMENTS

| | | |
|---|---|---|
| 3,858,437 | 1/1975 | Jarzynski et al. .................. 73/597 |
| 4,346,599 | 8/1982 | McLaughlin et al. .................. 73/597 |
| 4,754,645 | 7/1988 | Piche et al. .................. 73/597 |

OTHER PUBLICATIONS

Smith et al., "An Acoustic Microscope for Industrial Applications", *IEEE Transaction on Sonics & Ultrasonics*, SU-32, 1985.
Atalar, A., "An Angular-Spectrum Approach to Contrast in Reflection Acoustic Microscopy", *J. Appl. Phys.*, 49(10), Oct. 1978.
Adachi et al., "High Frequency Ultrasonic Studies of Polyethylene", *Polymer*, vol. 22, Aug. 1981.
Tsao et al., "Ultrasonic Imaging Analysis of Component Integrity", In Review of Progress in Quantitative Nondestructive Evaluation, vol. 3, Proc. of 10th Ann. Review, Santa Cruz, CA, 7-12 Aug. 1983.
Hartmann et al., "Immersion Apparatus for Ultrasonic Measurements in Polymers", *J. Acoust. Soc. Amer.*, vol. 56, #5 (Nov. '74).
Paddison, G. W., "An Ultrasonic Immersion Apparatus for the Determination of . . . ", Proc. IEEE Ultrasonics Symposium, 502-506 (1979).

*Primary Examiner*—Ian J. Lobo
*Attorney, Agent, or Firm*—Oblon, Spivak, McClelland, Maier & Neustadt

[57] ABSTRACT

An acoustic imaging method for nondestructive evaluation of materials comprises the steps of measuring the temperature dependence of the acoustic wave transmittance of the material in advance, cooling the material to a temperature at which its acoustic wave transmittance is high, and carrying out acoustic imaging.

7 Claims, 4 Drawing Sheets

ACOUSTIC IMAGING METHOD AND APPARATUS FOR NONDESTRUCTIVE EVALUATION OF MATERIALS

BACKGROUND OF THE INVENTION

1. Field of the Invention

This invention relates to an acoustic imaging method and apparatus for use in nondestructively inspecting polymer materials in order to determine their reliability and the like.

2. Prior Art Statement

The use of the acoustic imaging method for nondestructive evaluation of materials is not new. However, depending on the material being evaluated and particularly in the case of polymer materials, the attenuation of the high frequency acoustic waves passed through the material is so large as to make use of the acoustic imaging method extremely difficult. Moreover, the attenuation of the acoustic waves increases with increasing frequency. Thus in the inspection of materials exhibiting high attenuation, it has generally been the practice to employ low-frequency acoustic waves. This is disadvantageous, however, since the longer wavelength of low-frequency acoustic waves lowers the resolution with which defects and structural details of the material can be observed.

Nowadays a large amount of bonding is being used in structural materials for aircraft and automobiles, and the presence of bubbles and other defects at the bonded portions can lead to a serious decrease in the material strength. With conventional techniques it has been difficult to detect microdefects down to the smallest size (about 0.1 mm) which can lead to reduced strength. In such technical fields there has therefore arisen an urgent need for an improvement in inspection sensitivity and resolution.

On the other hand, it has been discovered that when a polymer material or a composite material containing a polymer is cooled from room temperature to around −100°) C., it may within specific temperature ranges exhibit a marked decrease the viscoelasticity that is the cause of acoustic waves attenuation. Moreover, since the speed of sound also varies greatly with temperature, in some bonded structures there can be expected to be observed an improvement in acoustic impedance matching.

The present invention was accomplished on the basis of the aforesaid knowledge and one object thereof is to provide an acoustic imaging method for imaging materials which takes advantage of the temperature dependence of the acoustic transmittance of the material for increasing sensitivity and resolution in acoustic imaging. Another object of the invention is to provide an apparatus for carrying out this method.

SUMMARY OF THE INVENTION

For achieving the aforesaid objects, the present invention provides an acoustic imaging method for nondestructive evaluation of materials in which the temperature dependence of the acoustic wave transmittance of the material is measured in advance and acoustic imaging is carried out with the material cooled to a temperature at which its acoustic wave transmittance is high. More specifically, a temperature controller capable of varying the temperature of the material over a broad range is used for measuring the temperature dependence of the acoustic wave transmittance of the material in advance, the material is then held at a temperature at which it is known from this measurement to exhibit high transmittance, acoustic waves are emitted toward the material, and the echo from the material is used to obtain an image. This method makes it possible to use acoustic waves of a frequency of the order of tens of MHz even with a material exhibiting high acoustic wave attenuation. The use of acoustic waves of the order of tens of MHz enhances the sensitivity and resolution of the imaging and makes it possible to obtain a clear image of the material at a prescribed depth thereof, thus enabling easy detection of microdefects present in the material.

The above and other features of the present invention will become apparent from the following description made with reference to the drawings.

DETAILED DESCRIPTION OF THE PREFERRED EMBODIMENT

Figure 1:
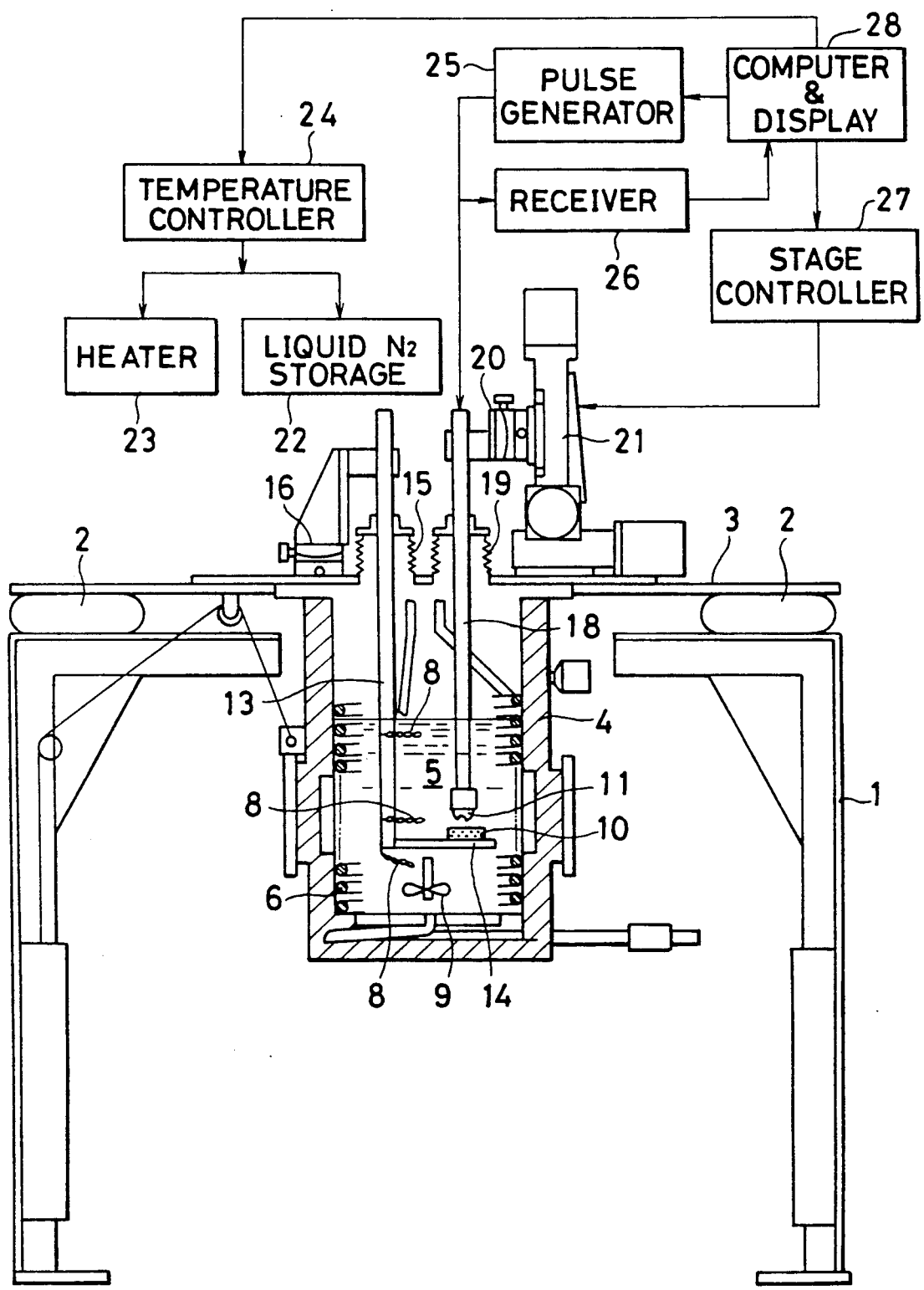
FIG. 1 is a schematic view of an embodiment of the acoustic imaging apparatus according to the present invention.

Referring to the embodiment of the acoustic imaging apparatus schematically illustrated in FIG. 1, a frame 3 is supported on the top of a base 1 via an air damper 2 and the equipment required for acoustic imaging (a pulse generator 25, a receiver 26, a stage controller 27 and a computer and display 28, all of which are of the conventional type) is mounted on the frame 3. A sealed cell 4 supported on the frame 3 contains methanol or other such appropriate acoustic wave coupler 5. A helical pipe 6 used for passage of liquid nitrogen and having the heating wire of a heater 23 wrapped thereabout is disposed within the acoustic wave coupler 5 along the inner wall of the sealed cell 4. The apparatus is equipped with a temperature controller 24 which by controlling the supply of liquid nitrogen to the helical pipe 6 from a liquid nitrogen tank 22 and the amount of heat generated by the heating wire is able to adjust the temperature of the acoustic wave coupler 5 between approximately room temperature and −100° C. As a result, a specimen 10 of a material to be inspected can be cooled to and maintained at a prescribed temperature. The temperature of the acoustic wave coupler 5 is detected by three thermocouples 8 located at different positions. When the temperatures detected by the thermocouples 8 differ, the temperature controller operates a rotary stirrer 9 within the sealed cell 4 for agitating the acoustic wave coupler 5 and causing its temperature to become uniform throughout. An acoustic transducer 11 is disposed within the acoustic wave coupler 5 in the sealed cell 4 so as to face the specimen 10. The specimen 10 is attached to a specimen mount 14 at the lower end of a support rod 13. The support rod 13 extends upwardly through a soft bellows 15 to the exterior of the sealed cell 4 and has its upper end attached to a tilt adjustor 16 supported on the frame 3. The acoustic transducer 11 is attached to the lower end of a rod 18 which extends upwardly through a soft bellows 19 to the exterior of the sealed cell 4 and has its upper end attached to a three-axis stage 21 via a tilt adjustor 20.

The angle between the specimen 10 and the acoustic transducer 11 disposed in facing relationship therewith can thus be adjusted by the tilt adjustors 16, 20 and the three-axis stage 21 can be driven by the stage controller 27 so as to cause the acoustic transducer 11 to scan the surface of the specimen 10.

The acoustic imaging by the aforesaid apparatus is conducted under the control of the computer 28.

More specifically, the computer 28 controls the pulse generator 25 causing it to generate high-frequency pulses. These pulses are sent to the acoustic transducer 11, which in response propagates acoustic waves into the acoustic wave coupler 5 in the direction of the specimen 10. The acoustic wave echo from the specimen 10 is received by the acoustic transducer 11 and then sent through the receiver 26 to the computer 28 for imaging and display on a CRT or the like. During this imaging process, the computer 28 controls the stage controller 27, and the stage controller 27 in turn controls the three-axis stage 21 so as to cause the acoustic transducer 11 to scan the specimen 10 two-dimensionally. Therefore, if any portion that is affected by the propagated acoustic wave is present in the specimen 10, it will produce a pattern and be imaged. It thus becomes possible to non-destructively inspect the material.

The computer 28 also controls the temperature controller 24 for maintaining an appropriate balance between the supply of liquid nitrogen from the liquid nitrogen tank 22 and the amount of heat produced by the heater 23 so as to maintain the acoustic wave coupler 5 at a prescribed temperature.

For determining the temperature dependence of the acoustic transmittance of the specimen 10, the computer 28 progressively varies the temperature to which the acoustic wave coupler 5 is cooled, thereby indirectly varying the temperature to which the specimen 10 is cooled, and measures the change in the acoustic transmittance of the specimen 10 with temperature. This measurement is conducted by, for example, measuring the amplitude of acoustic wave echoes and the result is output as a function of temperature.

In conducting nondestructive evaluation of a sample using the acoustic imaging apparatus of the foregoing arrangement, control is conducted by the computer 28 so as to measure the acoustic transmittance of the specimen 10 as the temperature controller 24 is operated for varying the temperature of the specimen 10 over a wide temperature range, the so-obtained temperature dependence of the acoustic transmittance of the specimen 10 is used as the basis for maintaining the specimen 10 at a temperature at which it exhibits high acoustic transmittance, and acoustic waves are thereafter emitted in the direction of the specimen 10. Since the acoustic transmittance of the specimen 10 is high at this time, it becomes possible to use high-frequency acoustic waves for imaging the specimen at a specified depth. Thus while in the past it has been difficult to obtain a clear image of a high-attenuation material such as a polymer adhesive using high-frequency acoustic waves of the order of tens of MHz because the attenuation grows larger with increasing frequency, in accordance with the present invention it becomes possible to reduce the attenuation within the material, detect bubbles and defects down to the smallest size (about 0.1 mm) having an effect on the strength of an adhesive and to obtain clear images at specified depths of the material.

The inspection method according to this invention is appropriate for use with polymer materials whose attenuation is high at room temperature but decreases with cooling. As specific examples can be mentioned epoxy resins, polycarbonate resins, polyolefine resins and the like.

If in conducting the imaging of the specimen it is found necessary to bring out particular image features with higher clarity, this can be accomplished by carrying out differentiation processing or the like between a plurality of images obtained under different temperature conditions. For example, the images of specimen portions exhibiting low temperature dependence can be eliminated so as to image the defect portions exhibiting high temperature dependence with enhanced clarity and thus increase the defect detection sensitivity.

An example of the method according to this invention will now be explained.

The method of the invention was worked using an apparatus of the arrangement shown in FIG. 1. The sealed cell 4 measured 20 cm in diameter and 20 cm in depth and was partially filled with methanol as the medium for acoustic wave propagation (the acoustic wave coupler 5). The helical pipe 6 wrapped with a heating wire was disposed in the methanol along the inner surface the sealed cell 4. Liquid nitrogen was passed through the helical pipe 6 and heat was generated by the heating wire so as to make it possible to maintain the acoustic wave coupler 5 and thus the specimen 10 at a temperature between about room temperature and $-100°$ C.

The stirrer 9 provided near the bottom of the sealed cell 4 was operated to stir the coupler 5, whereby it was possible to maintain the temperature difference in the coupler within the sealed cell between about 10° C. and 0.4° C. The temperature of the coupler was measured by the thermocouples disposed one each in the vicinity of the stirrer 9, in the vicinity of the specimen and in the upper region of the coupler.

While the speed of acoustic waves is approximately the same in methanol and ethanol, methanol is a better acoustic wave coupler since its acoustic wave attenuation is only about half that of ethanol. Where the specimen has low resistance to alcohols, however, it is necessary to use some other liquid coupler.

Figure 2:
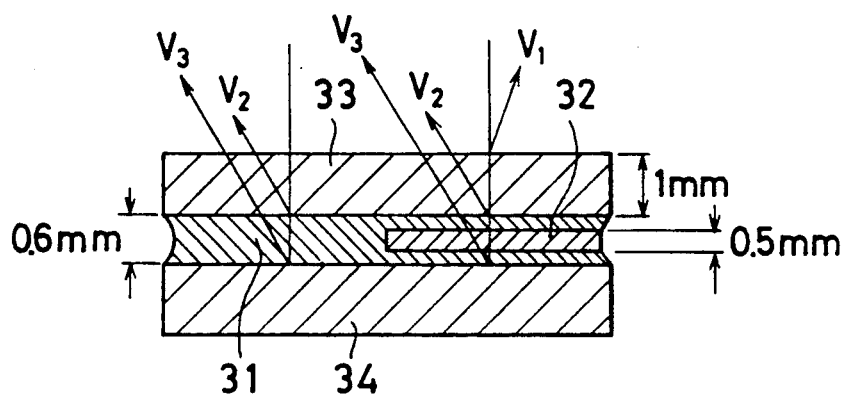
FIG. 2 is a sectional view of a material specimen used in a test.

The specimen used is shown in FIG. 2. It was formed as a sandwich-like structure consisting of an epoxy adhesive 31 (Grace Japan K.K.: Eccobond 285 with #24LV catalyst) between two acrylic plates 33, 34 and a 0.5 mm thick polyethylene sheet 32 further partially embedded within the epoxy adhesive 31 (on the right side in the drawing).

Figure 3:
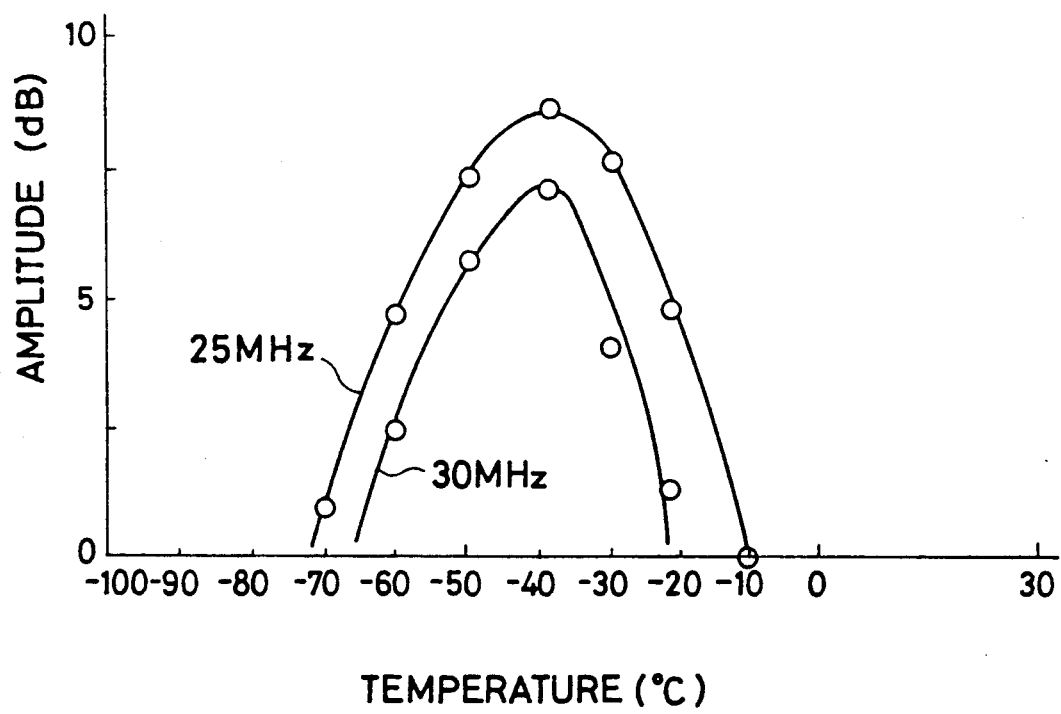
FIG. 3 is a graph showing the temperature dependence of the amplitude of an acoustic wave echo reflected from epoxy resin in the specimen of FIG. 2.

Prior to imaging, an acoustic lens having a focal length of 12.7 mm was used to measure the temperature dependence (at the focal plane) of the maximum amplitude of the echo ($V_3$) from the bottom surface of the epoxy adhesive 31. The results are shown in FIG. 3, from which it will be noted that the amplitude rose rapidly with decreasing temperature from around $-20°$ C. for both 25 MHz and 30 MHz acoustic waves. The main cause for this variation in amplitude is thought to be that the attenuation of the acoustic waves by the epoxy adhesive layer decreased markedly with cooling. The change in impedance matching at the interface with the acrylic plate 34 caused by the change in the propagation speed of the acoustic waves was 1.9 dB and thus can be presumed to have contributed little to the variation in amplitude. The amplitude of the echo $V_3$ diminished again when the specimen was further cooled to below $-70°$ C. This is presumed to be due to increased attenuation in the acoustic wave coupler.

From the data obtained in the foregoing manner it was thus determined that the temperature range in which the acoustic transmittance is high extends between about $-20°$ C. and $-60°$ C.

Based on this knowledge, a 25 MHz acoustic wave was directed toward the specimen 10 and the echo $V_2$ from the top surface of the layer of epoxy adhesive 31 and the echo $V_3$ from the bottom surface thereof were imaged. FIG. 4 shows the images of the specimen obtained from the echo $V_2$, while FIG. 5 shows the images obtained from the echo $V_3$. In these photographically recorded images, the left half corresponds to the epoxy adhesive layer only and the right half corresponds to the portion where the polyethylene sheet is embedded in the epoxy adhesive layer.

Figure 4A:
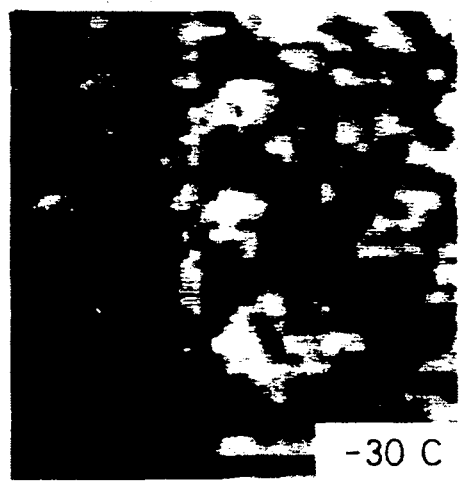
FIGS. 4($a$), 4($b$) and 4($c$) show images obtained based on echoes reflected from the top surface of the epoxy resin in the specimen when the temperature of the epoxy resin was −30° C., −50° C. and +20° C., respectively.
Figure 4B:
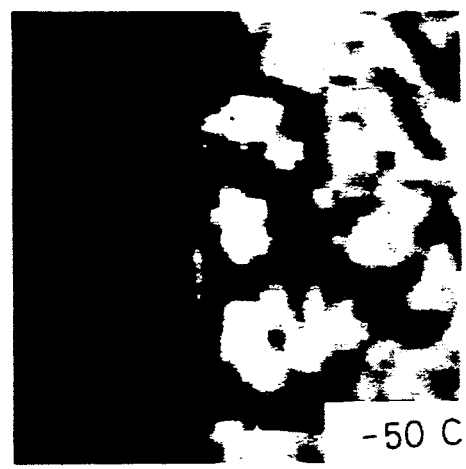
Figure 4C:
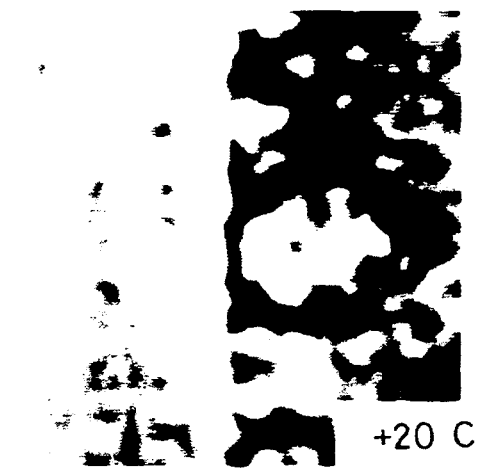

FIG. 4(a) shows the image obtained when the specimen was cooled to $-30°$ C. In this image it is possible to discern the epoxy resin layer and small particles of epoxy resin that infiltrated the polyethylene sheet side. That the image obtained at $+20°$ C. shown in FIG. 4(c) corresponds to the same region can be confirmed from the similar shape of the small epoxy particles.

Figure 5A:
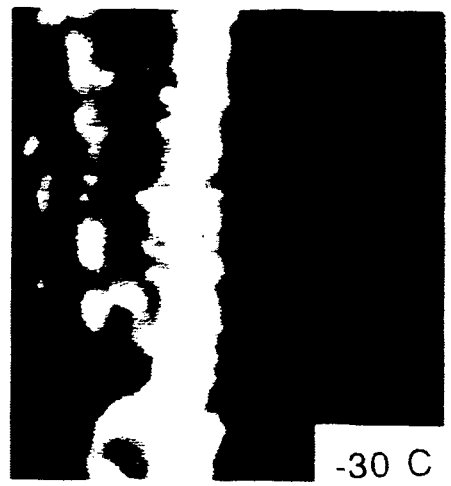
FIGS. 5($a$), 5($b$) and 5($c$) show images obtained based on echoes reflected from the bottom surface of the epoxy resin in the specimen when the temperature of the epoxy resin was −30° C., −50° C. and +20° C., respectively.
Figure 5B:
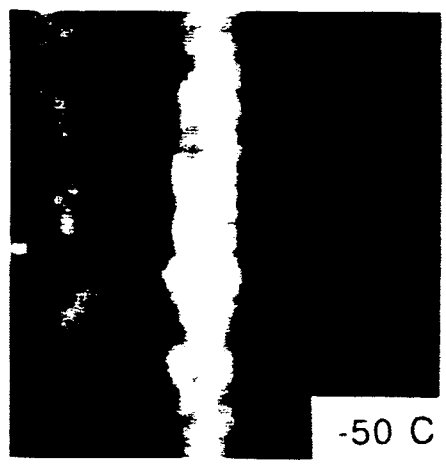
Figure 5C:
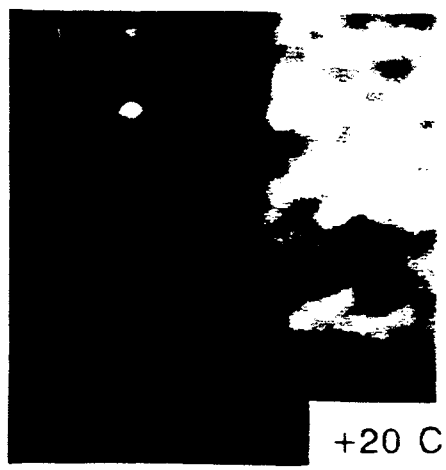

FIG. 5(a) shows the image obtained when the specimen was cooled to $-30°$ C. From a comparison of this image with the image obtained at $+20°$ C. shown in FIG. 5(c), it is clear that while it was not possible to obtain a meaningful image at $+20°$ C. because of the large attenuation and the resulting weak echo signal received at this temperature, the image obtained at $-30°$ C. enables observation on the left side thereof of bubbles and nonuniformities in the layer of epoxy adhesive 31 which are presumed to have an adverse effect on the structural integrity of the bonding material. FIG. 5(b) shows the image obtained when the specimen was cooled to $-50°$ C. As in the case of FIG. 5(a), the state of the layer of epoxy adhesive 31 can be clearly observed.

Thus, in accordance with this invention, by imaging the specimen after it has been cooled to a temperature region where it exhibits low attenuation, it becomes possible to use high-frequency acoustic waves which enable imaging and observation of minute features not observable at room temperature. The invention is thus highly effective for the detection of tiny bubbles, scratches and other microdefects.

As will be noted from the right halves of the photographs, it was not possible to obtain useful images of the portion of the specimen where the polyethylene sheet 32 was present. This is due to the high attenuation of the acoustic waves by the polyethylene sheet and it is considered necessary to conduct cooling to still lower temperatures for obtaining a clear image of this portion.

In the foregoing example, a high-precision temperature controller was used in order to demonstrate the effectiveness of cooling the specimen. Since the temperature range over which the attenuation becomes markedly low is relatively broad, however, it is possible in an apparatus for practical application to use a simpler and less expensive temperature controller without substantially decreasing the effect realized. For example, in cases where it is possible to employ an electronic scanning type acoustic imaging apparatus, the measurement of the temperature dependence of the acoustic transmittance of the specimen, the maintaining of the specimen temperature within a range at which its acoustic transmittance becomes high, the scanning of the surface of the specimen with acoustic waves and the imaging of the specimen using the acoustic wave echo can all be conducted while the specimen is simply being sprayed with a low-temperature gas.

As explained in the foregoing, by taking advantage of the fact that the acoustic transmittance of the specimen is temperature dependent, the present invention enables an improvement in acoustic imaging sensitivity and resolution by the simple expedient of controlling the temperature of the specimen so as to control its acoustic properties.

What is claimed is:

1. An acoustic imaging method for nondestructive evaluation of materials, comprising the steps of:
    measuring a temperature dependence of acoustic wave transmittance of a material from an echo reflected from the inside of the material when the material is irradiated with converged acoustic waves while being cooled;
    using the measured temperature dependence to determine a temperature at which the acoustic wave transmittance of the material becomes higher than that assumed before the material is cooled;
    cooling the material to said determined temperature;
    emitting converged acoustic waves toward the cooled material;
    receiving an echo reflected from the inside of the material; and
    using the echo to image the material at a prescribed depth.

2. An acoustic imaging method according to claim 1, wherein the material is a polymer.

3. An acoustic imaging method according to claim 1, wherein the converged acoustic waves emitted toward the material have a frequency of the order of tens of Mhz.

4. An acoustic imaging method according to claim 1, further comprising the step of immersing the material in an acoustic wave propagation medium.

5. An acoustic imaging apparatus for nondestructive evaluation of materials, comprising:
    first means for cooling a material to and holding the same at a prescribed temperature;
    a transducer provided with an acoustic lens and disposed to face the material;
    means for measuring variation in an acoustic transmittance of the material with temperature while the material is cooled to different temperatures by the first means;
    second means responsive to a signal from the measuring means, for cooling the material to a temperature at which the acoustic transmittance of the material becomes higher than that assumed before the material is cooled by the first means; and
    means for causing the transducer to emit converged acoustic waves toward the cooled material, receiving an echo reflected from the inside of the material and using the echo to image the material at a prescribed depth.

6. An acoustic imaging apparatus according to claim 5, wherein the material is a polymer.

7. An acoustic imaging apparatus according to claim 5, wherein the transducer emits acoustic waves of a frequency of the order of tens of MHz.

* * * * *

UNITED STATES PATENT AND TRADEMARK OFFICE
CERTIFICATE OF CORRECTION

PATENT NO. : 5,101,382
DATED     : March 31, 1992
INVENTOR(S) : Kazushi Yamanaka It is certified that error appears in the above-identified patent and that said Letters Patent is hereby corrected as shown below:

Title page, item [73] Assignee: should read --Agency of Industrial Science & Technology, Ministry of International Trade & Industry--

Signed and Sealed this

Twenty-second Day of June, 1993

Attest:

MICHAEL K. KIRK

*Attesting Officer*   *Acting Commissioner of Patents and Trademarks*